US008436213B2

(12) United States Patent
Dakka et al.

(10) Patent No.: US 8,436,213 B2
(45) Date of Patent: May 7, 2013

(54) PROCESS FOR PRODUCING PHENOL AND METHYL ETHYL KETONE

(75) Inventors: Jihad M. Dakka, Whitehouse Station, NJ (US); Jane C. Cheng, Bridgewater, NJ (US); John S. Buchanan, Lambertville, NJ (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 177 days.

(21) Appl. No.: 13/060,335

(22) PCT Filed: Aug. 4, 2009

(86) PCT No.: PCT/US2009/052631
§ 371 (c)(1), (2), (4) Date: Feb. 23, 2011

(87) PCT Pub. No.: WO2010/042269
PCT Pub. Date: Apr. 15, 2010

(65) Prior Publication Data
US 2011/0160489 A1    Jun. 30, 2011

(51) Int. Cl.
*C07C 45/53* (2006.01)
*C07C 37/08* (2006.01)
*C07C 2/70* (2006.01)
*C07C 4/12* (2006.01)

(52) U.S. Cl.
USPC ........... 568/385; 568/768; 568/798; 585/461; 585/486

(58) Field of Classification Search .................. 568/385, 568/768, 798; 485/461
See application file for complete search history.

(56) References Cited

U.S. PATENT DOCUMENTS

| | | |
|---|---|---|
| 2,584,103 A | 2/1952 | Pines et al. |
| 3,755,194 A | 8/1973 | Avilov et al. |
| 3,819,735 A | 6/1974 | Argento et al. |
| 3,974,095 A | 8/1976 | Volpin et al. |
| 4,051,191 A | 9/1977 | Ward |
| 4,320,242 A | 3/1982 | Onodera et al. |
| 4,329,509 A | 5/1982 | Haag et al. |
| 4,459,426 A | 7/1984 | Inwood et al. |
| 4,468,475 A | 8/1984 | Kuehl |
| 4,490,565 A | 12/1984 | Chang et al. |
| 4,490,566 A | 12/1984 | Chang et al. |
| 4,517,390 A | 5/1985 | Russell et al. |
| 4,891,458 A | 1/1990 | Innes et al. |
| 4,992,606 A | 2/1991 | Kushnerick et al. |
| 5,057,206 A | 10/1991 | Engel et al. |
| 5,059,736 A | 10/1991 | Tamura et al. |
| 5,077,445 A | 12/1991 | Le |
| 5,081,323 A | 1/1992 | Innes et al. |
| 5,149,894 A | 9/1992 | Holtermann et al. |
| 5,177,283 A | 1/1993 | Ward |
| 5,183,945 A | 2/1993 | Stibrany et al. |
| 5,298,667 A | 3/1994 | Iwanaga et al. |
| 5,334,795 A | 8/1994 | Chu et al. |
| 5,336,820 A | 8/1994 | Owen et al. |
| 5,371,310 A | 12/1994 | Bennett et al. |
| 5,476,958 A | 12/1995 | Mautner et al. |
| 5,557,024 A | 9/1996 | Cheng et al. |
| 5,723,710 A | 3/1998 | Gajda et al. |
| 5,779,882 A | 7/1998 | Chester et al. |
| 5,811,623 A * | 9/1998 | Ryu et al. ................... 585/671 |
| 5,922,920 A | 7/1999 | Bond et al. |
| 6,002,057 A | 12/1999 | Hendriksen et al. |
| 6,051,521 A | 4/2000 | Cheng et al. |
| 6,156,694 A | 12/2000 | Harper |
| 6,169,215 B1 | 1/2001 | Levin et al. |
| 6,169,216 B1 | 1/2001 | Levin et al. |
| 6,297,406 B1 | 10/2001 | Levin et al. |
| 6,313,362 B1 | 11/2001 | Green et al. |
| 6,410,804 B1 | 6/2002 | Levin et al. |
| 6,440,886 B1 | 8/2002 | Gajda et al. |
| 6,717,025 B1 | 4/2004 | Risch et al. |
| 6,720,462 B2 | 4/2004 | Kuhnle et al. |
| 6,852,893 B2 | 2/2005 | Kuhnle et al. |
| 6,911,568 B1 | 6/2005 | Dandekar et al. |
| 2003/0028060 A1 | 2/2003 | Dandekar et al. |
| 2003/0083527 A1 | 5/2003 | Kuhnle et al. |
| 2004/0059167 A1 | 3/2004 | Clark et al. |
| 2006/0009666 A1 | 1/2006 | Ramachandran et al. |

(Continued)

FOREIGN PATENT DOCUMENTS

| | | |
|---|---|---|
| EP | 0 543 619 | 5/1993 |
| EP | 0 578 194 | 1/1994 |

(Continued)

OTHER PUBLICATIONS

Georgiev et al., "*Dealkylation of Alkyl-Substituted Aromatic Hydrocarbons in Presence of an Aluminum Silicate Catalyst Communication 1. Kinetics of the Dealkylation of Monoalklbenzenes*", Russian Chemical Bulletin, 1959, vol. 8, No. 3, pp. 463-470.

Isakov et al., "*Catalytic Properties of Palladium-Zeolite Systems in the Synthesis of Sec-Butylbenzene From Benzene and Ethylene*", Inst. Org. Khim, im. N. D. Zelinskogo, Moscow, Russia, Neftekhimiya, 1994, vol. 34, No. 2, pp. 151-170 (Abstract Only; XP002317126).

Isakov et al., "*Study of Polyfunctional Zeolite Catalysts. Communication 2. Formation of a Catalyst for Synthesis Off Sec-Butylbenzene Prepared From Nickel Acetylacetonate and Cay Zeolite*", Inst. Org. Khim. im. Zelinskogo, Moscow, USSR, Izv. Akad Nauk SSSR, Ser. Khim. 1976, vol. 3, pp. 498-504 (Abstract Only).

(Continued)

*Primary Examiner* — Sikarl Witherspoon
(74) *Attorney, Agent, or Firm* — Anthony G. Boon; Jamie L. Sullivan; Siwen Chen

(57) ABSTRACT

In a process for reducing the level of tert-butylbenzene in a mixed butylbenzene feed comprising tert-butylbenzene and sec-butylbenzene, the feed is contacted under dealkylation conditions with a catalyst system comprising a dealkylation catalyst whereby the tert-butylbenzene is selectively dealkylated to produce an effluent stream which comprises benzene and which has a lower concentration of tert-butylbenzene than said feed.

16 Claims, 2 Drawing Sheets

U.S. PATENT DOCUMENTS

| | | |
|---|---|---|
| 2006/0178544 A1 | 8/2006 | Murray et al. |
| 2006/0211901 A1 | 9/2006 | Boyer et al. |
| 2008/0086018 A1 | 4/2008 | Cheng et al. |
| 2008/0154082 A1 | 6/2008 | Dandekar et al. |
| 2009/0306433 A1 | 12/2009 | Dakka et al. |

FOREIGN PATENT DOCUMENTS

| | | |
|---|---|---|
| EP | 1 088 809 | 4/2001 |
| FR | 2 182 802 | 12/1973 |
| GB | 844242 | 8/1960 |
| JP | 2002-282698 | 10/2002 |
| SU | 417405 | 8/1974 |
| SU | 372903 | 10/1974 |
| SU | 265349 | 10/1976 |
| SU | 1245564 | 7/1986 |
| WO | 02/088051 | 11/2002 |
| WO | 2004/052810 | 6/2004 |
| WO | 2006/015824 | 2/2006 |
| WO | 2006/015826 | 2/2006 |
| WO | 2007/093362 | 8/2007 |
| WO | 2008/098676 | 8/2008 |

OTHER PUBLICATIONS

Minachev et al., "*Alkylation of Benzene by Ethylene on Catalysts Produced From Synthetic Zeolites Ultrasil*", Inst. Org. Khim, im. Zelinskogo, Moscow, USSR, Neftekhimiya, 1988, vol. 28, No. 2, pp. 151-158 (Abstract Only: XP-002317128).

Minachev et al., "*Bifunctional Catalysts for the Alkylation of Aromatic Compounds by Ethylene*", USSR, Lektsii-Vses, Shk. Katal, 1981, vol. 2, pp. 76-111 (Abstract Only: XP-002317129).

Minachev et al., "*Preparation of Secondary Butylbenzene From Ethylene and Benzene*", IOKh im. Zelinskogo, USSR, Neftepererabotka I Neftekhimiya, Moscow, Russian Federation, 1971, vol. 9, pp. 24-27 (Abstract Only: XP-002317127).

Minachev et al., "*Study of the Nature of Bifunctional Catalysts for the Synthesis of Sec-Butylbenzene From Ethylene and Benzene*", Inst. Org. Khim, im. Zelinskogo, Moscow, USSR, Geterog. Katal., $4^{th}$ Edition, 1979, Pt. 2, pp. 485-492 (Abstract Only).

Ohkubo et al., "*A Kinetic Study on the Homogeneous Liquid-Phase Oxidation of Cumene in the Presence of Tripheylsulfonium Chloride*", Bull. Chem. Soc., Japan, 1969, vol. 42, No. 7, pp. 1800-1806.

Sachanen et al., "*High-Temperature Alkylation of Aromatic Hydrocarbons*", Ind. Eng. Chem., 1941, vol. 33, No. 12, pp. 1540-1544.

Sheldon et al., "*Organocatalytic Oxidations Mediated by Nitroxyl Radicals*", Adv. Synth. Catal., 2004, vol. 346, pp. 1051-1071.

Sidorov et al., "*Alkylation of Benzene With Olefins*", Sernaya Kislota Protsessakh Neftekhim, 1975, pp. 172-177.

Van Sickle et al., "*Liquid-Phase Oxidations of Cyclic Alkenes*", JACS, 1965, vol. 87, No. 21, pp. 4824-4832.

Van Sickle et al., "*Oxidations of Acyclic Alkenes*", JACS, 1967, vol. 89, No. 4, pp. 967-977.

Yen, "*Phenol*", Process of Economics Report, Stanford Research Institute, 1977, pp. 112-121 and 261-263.

* cited by examiner

PROCESS FOR PRODUCING PHENOL AND METHYL ETHYL KETONE

PRIORITY CLAIM

This application is a National Stage Application of International Application No. PCT/US2009/52631 filed Aug. 4, 2009, which claims the benefit of prior U.S. provisional application Ser. No. 61/104,294 filed Oct. 10, 2008, both of which are hereby incorporated by reference in their entirety.

CROSS-REFERENCE TO RELATED APPLICATIONS

This application is related to U.S. Pat. Nos. 7,671,248; 7,812,196; 7,799,956; 7,834,218; and International Patent Cooperation Treaty Application No. PCT/EP2007/001205, filed Feb. 8, 2007.

FIELD OF THE INVENTION

The present invention relates to a process for co-producing phenol and methyl ethyl ketone.

BACKGROUND OF THE INVENTION

Phenol and methyl ethyl ketone are important products in the chemical industry. For example, phenol is useful in the production of phenolic resins, bisphenol A, ε-caprolactam, adipic acid, alkyl phenols, and plasticizers, whereas methyl ethyl ketone can be used as a lacquer, a solvent and for dewaxing of lubricating oils.

The most common route for the production of methyl ethyl ketone is by dehydrogenation of sec-butyl alcohol (SBA), with the alcohol being produced by the acid-catalyzed hydration of butenes. For example, commercial scale SBA manufacture by reaction of butylene with sulfuric acid has been accomplished for many years via gas/liquid extraction.

Currently, the most common route for the production of phenol is the Hock process. This is a three-step process in which the first step involves alkylation of benzene with propylene to produce cumene, followed by oxidation of the cumene to the corresponding hydroperoxide and then cleavage of the hydroperoxide to produce equimolar amounts of phenol and acetone. However, the world demand for phenol is growing more rapidly than that for acetone. In addition, the cost of propylene relative to that for butenes is likely to increase, due to a developing shortage of propylene. Thus, a process that uses butenes instead of propylene as feed and co-produces methyl ethyl ketone rather than acetone may be an attractive alternative route to the production of phenol.

It is known that phenol and methyl ethyl ketone can be co-produced by a variation of the Hock process in which sec-butylbenzene is oxidized to obtain sec-butylbenzene hydroperoxide and the peroxide decomposed to the desired phenol and methyl ethyl ketone. An overview of such a process is described in pages 113-241 and 261-263 of Process Economics Report No. 22B entitled "Phenol", published by the Stanford Research Institute in December 1977.

In addition, it is known that sec-butylbenzene can be produced by alkylating benzene with n-butenes over an acid catalyst. For example, in our International Patent Publication No. WO06/015826, we have described a process for producing phenol and methyl ethyl ketone, in which benzene is initially contacted with a $C_4$ alkylating agent under alkylation conditions with a catalyst comprising zeolite beta or a molecular sieve of the MCM-22 family to produce an alkylation effluent comprising sec-butylbenzene. The sec-butylbenzene is then oxidized to produce a hydroperoxide and the hydroperoxide is decomposed to produce phenol and methyl ethyl ketone. The oxidation step can be conducted with or without a catalyst under conditions including a temperature between about 70° C. and about 200° C., such as about 90° C. to about 130° C., and a pressure of about 0.5 to about 10 atmospheres (50 to 1000 kPa). Suitable catalysts are said to include the N-hydroxy substituted cyclic imides described in Published U.S. Patent Application No. 2003/0083527.

Although the chemistry involved in the alkylation of benzene with butenes is very similar to ethylbenzene and cumene production, as the carbon number of the alkylating agent increases, the number of product isomers also increases. For example, ethylbenzene has one isomer, propylbenzene has two isomers (cumene and n-propylbenzene), and butylbenzene has four isomers (n-, iso-, sec-, and t-butylbenzene). For sec-butylbenzene production, it is important to minimize n-, iso-, t-butylbenzene, and phenylbutenes by-product formation since these by-products have boiling points very close to sec-butylbenzene and hence are difficult to separate from sec-butylbenzene by distillation (see table below).

| Butylbenzene | Boiling Point, ° C. |
|---|---|
| t-Butylbenzene | 169 |
| i-Butylbenzene | 171 |
| s-Butylbenzene | 173 |
| n-Butylbenzene | 183 |

By-product formation can of course be minimized by using a pure n-butene feed, but in practice it is desirable to employ more economical butene feeds, such as Raffinate-2, to produce sec-butylbenzene. A typical Raffinate-2 contains 0-1% butadiene and up to 5% isobutene. With this increased isobutene level in the feed, a higher by-product make is expected even with a highly selective alkylation catalyst.

Moreover, iso-butylbenzene and especially tert-butylbenzene are known to be inhibitors to the oxidation of sec-butylbenzene to the corresponding hydroperoxide, a necessary next step for the production of methyl ethyl ketone and phenol. Even in the presence of catalysts such as cyclic imides, these impurities are found to decrease the selectivity to sec-butylbenzene hydroperoxide while themselves being oxidized at a much slower rate than sec-butylbenzene. Thus, since oxidation is generally operated at low conversion rates with recycle of unreacted sec-butylbenzene, impurities such as iso-butylbenzene and tert-butylbenzene are likely to build up in the recycle stream.

Thus any successful commercial process for producing phenol via alkylation of benzene to sec-butylbenzene is likely to require provision for reducing at least the level of tert-butylbenzene and preferably the level of iso-butylbenzene in the alkylation effluent.

Thermodynamic calculations suggest that iso-butylbenzene and particularly tert-butylbenzene can be dealkylated at a faster rate than sec-butylbenzene. Thus, according to the present invention, a process is provided for reducing the level of tert-butylbenzene and, if present, iso-butylbenzene in a mixed butylbenzene feed, such as that generated in the alkylation of benzene with Raffinate-2, by subjecting the feed to catalytic dealkylation. The dealkylation is found to selectively convert the tert-butylbenzene and iso-butylbenzene in the feed to benzene and iso-butene, with the latter reacting with the butylbenzenes in the feed to produce dibutylbenzenes or, in the presence of hydrogen, being reduced to isobutane. The benzene and dibutylbenzenes or iso-butane can readily be removed from the dealkylation effluent by distillation and the unconverted $C_{10}$ stream, which is rich in sec-butylbenzene as compared with the feed, can then be fed to the oxidation step.

SUMMARY OF THE INVENTION

In one aspect, the invention resides in a process for reducing the level of tert-butylbenzene in a mixed butylbenzene feed comprising tert-butylbenzene and sec-butylbenzene, the process comprising contacting the feed under dealkylation conditions with a catalyst system comprising a dealkylation catalyst whereby the tert-butylbenzene is selectively dealkylated to produce an effluent stream which comprises benzene and which has a lower concentration of tert-butylbenzene than said feed.

In one embodiment, the feed contains up to 50 wt % tert-butylbenzene and the effluent stream contains less than 5 wt % tert-butylbenzene.

Conveniently, said feed also comprises iso-butyl benzene and said contacting selectively dealkylates the iso-butylbenzene such that said effluent stream has a lower concentration of iso-butyl benzene than said feed.

Conveniently, the dealkylation catalyst comprises at least one of ZSM-5, zeolite beta, zeolite Y, zeolite X and a molecular sieve of the MCM-22 family.

Conveniently, said contacting is conducted in the presence of hydrogen and the catalyst system further comprises a hydrogenation metal such that iso-butene produced in the selective dealkylation of said tert-butylbenzene is at least partially hydrogenated to produce iso-butane.

Alternatively, said catalyst system further comprises an oligomerization catalyst such that iso-butene produced in the selective dealkylation of said tert-butylbenzene is at least partially oligomerized.

Conveniently, the dealkylation conditions include a temperature of about 130° C. and about 260° C., a pressure of about 100 kPa to about 1000 kPa and hydrogen to hydrocarbon molar ratio of 0 to about 1000.

In another aspect, the invention resides in a process for producing phenol and methyl ethyl ketone, the process comprising:

(a) contacting benzene and a $C_4$ olefin stream under alkylation conditions and in the presence of an alkylation catalyst to produce an alkylation effluent comprising sec-butylbenzene, iso-butyl benzene and tert-butylbenzene;

(b) contacting at least a portion of said alkylation effluent under dealkylation conditions with a catalyst system comprising a dealkylation catalyst whereby iso-butylbenzene and tert-butylbenzene in said at least a portion of said alkylation effluent are selectively dealkylated to produce a dealkylation effluent which comprises benzene and unreacted sec-butylbenzene and which has a lower concentration of iso-butylbenzene and tert-butylbenzene than said at least a portion of said alkylation effluent;

(c) oxidizing sec-butylbenzene in said dealkylation effluent to produce an oxidation effluent comprising sec-butylbenzene hydroperoxide;

(d) cleaving sec-butylbenzene hydroperoxide produced in (c) to produce phenol and methyl ethyl ketone; and (e) recycling at least part of the benzene from said dealkylation effluent to said contacting (a).

In a further aspect, the invention resides in a process for producing phenol and methyl ethyl ketone, the process comprising:

(a) contacting benzene and a $C_4$ olefin stream under alkylation conditions and in the presence of an alkylation catalyst to produce an alkylation effluent comprising sec-butylbenzene, iso-butylbenzene and tert-butylbenzene;

(b) oxidizing part of the sec-butylbenzene in said alkylation effluent to produce an oxidation effluent comprising sec-butylbenzene hydroperoxide, unreacted sec-butylbenzene, iso-butylbenzene and tert-butylbenzene;

(c) separating at least part of said sec-butylbenzene hydroperoxide from said oxidation effluent to leave a recycle stream comprising unreacted sec-butylbenzene, iso-butylbenzene and tert-butylbenzene;

(d) cleaving sec-butylbenzene hydroperoxide separated in said separating (c) to produce phenol and methyl ethyl ketone;

(e) contacting at least a portion of said recycle stream under dealkylation conditions with a catalyst system comprising a dealkylation catalyst whereby iso-butylbenzene and tert-butylbenzene in said at least a portion of said recycle stream are selectively dealkylated to produce a further effluent stream which comprises benzene and unreacted sec-butylbenzene and which has a lower concentration of iso-butylbenzene and tert-butylbenzene than said at least a portion of said recycle stream;

(f) recycling at least part of the benzene from said further effluent stream to said contacting (a); and (g) recycling at least part of the unreacted sec-butylbenzene from said further effluent stream to said oxidizing (b).

In one embodiment, said recycle stream is divided into a first portion, which is subjected to said contacting (e), and a second portion, which is recycled directly to said oxidizing (b).

Conveniently, the process further comprises hydrotreating said first recycle stream portion to remove oxygenates therefrom prior to said contacting (e).

In one embodiment, the process further comprises fractionating said further effluent stream to produce at least a benzene-rich fraction for said recycling (f) and a sec-butylbenzene-rich fraction for said recycling (g). Conveniently, said fractionating also produces a heavy fraction comprising dibutylbenzenes.

DETAILED DESCRIPTION OF THE EMBODIMENTS

Figure 1:
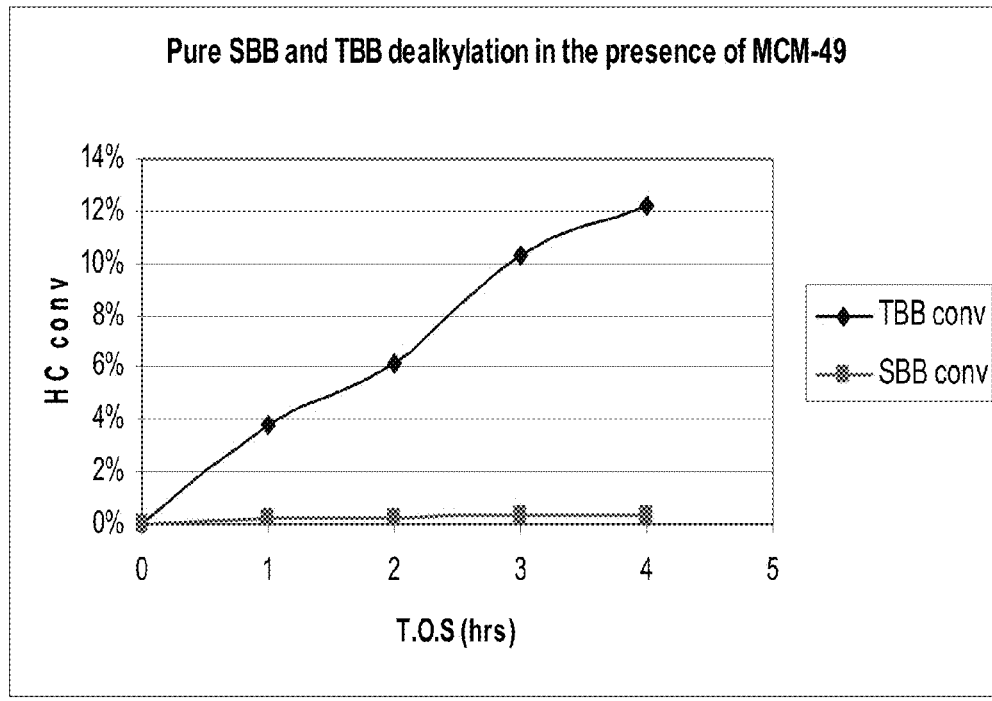
FIG. 1 is graph comparing the rate of hydrocarbon conversion with time on stream for the dealkylation of pure sec-butylbenzene in the presence of a MCM-49 catalyst in accordance with the process of Example 1 with the dealkylation of pure tert-butylbenzene in the presence of the same catalyst in accordance with the process of Example 2.

Described herein is a process for reducing the level of tert-butylbenzene and optionally iso-butylbenzene in a mixed butylbenzene feed containing sec-butylbenzene in addition to the tert-butylbenzene and/or iso-butylbenzene impurities. The process involves contacting the feed under dealkylation conditions with a catalyst system comprising a dealkylation catalyst such that the tert-butylbenzene and iso-butylbenzene in the feed are selectively dealkylated to produce an effluent stream having a lower concentration of tert-butylbenzene and iso-butylbenzene than the feed. The resultant effluent stream can then be used in the modified Hock process, in which the sec-butylbenzene is oxidized to sec-butylbenzene hydroperoxide and the peroxide is cleaved to produce phenol and methyl ethyl ketone. By subjecting the feed to the selective dealkylation step to reduce the level of the tert-butylbenzene and/or iso-butylbenzene impurities, it is found that the conversion rate and the sec-butylbenzene hydroperoxide selectivity of the oxidation step can be significantly improved.

Butylbenzene Feed

Any butylbenzene feed can be used in the present process provided the feed comprises at least sec-butylbenzene and tert-butylbenzene, optionally together with iso-butylbenzene. The sec-butylbenzene normally comprises the major component (at least 50 wt %) of the feed, although typically is present in an amount of at least 90 wt %, generally at least 95 wt %, of the overall feed. Similarly, although the total amount of tert-butylbenzene and iso-butylbenzene in the feed can be as high as 50 wt % or more of the total feed, each is generally present in an amount less than 5 wt %, such as between about 0.15 wt % and about 1.5 wt % of the feed.

The butylbenzene feed used in the present process is typically produced by alkylating benzene with a $C_4$ alkylating agent comprising at least one linear butene, namely butene-1, butene-2 or a mixture thereof. The alkylating agent can also be an olefinic $C_4$ hydrocarbon mixture containing linear butenes, such as can be obtained by steam cracking of ethane, propane, butane, LPG and light naphthas, catalytic cracking of naphthas and other refinery feedstocks and by conversion of oxygenates, such as methanol, to lower olefins.

For example, the following $C_4$ hydrocarbon mixtures are generally available in any refinery employing steam cracking to produce olefins; a crude steam cracked butene stream, Raffinate-1 (the product of remaining after solvent extraction or hydrogenation to remove butadiene from the crude steam cracked butene stream) and Raffinate-2 (the product remaining after removal of butadiene and isobutene from the crude steam cracked butene stream). Generally, these streams have compositions within the weight ranges indicated in Table 1 below.

TABLE 1

| Component | Crude $C_4$ stream | Raffinate 1 | | Raffinate 2 | |
|---|---|---|---|---|---|
| | | Solvent Extraction | Hydrogenation | Solvent Extraction | Hydrogenation |
| Butadiene | 30-85% | 0-2% | 0-2% | 0-1% | 0-1% |
| C4 acetylenes | 0-15% | 0-0.5% | 0-0.5% | 0-0.5% | 0-0.5% |
| Butene-1 | 1-30% | 20-50% | 50-95% | 25-75% | 75-95% |
| Butene-2 | 1-15% | 10-30% | 0-20% | 15-40% | 0-20% |
| Isobutene | 0-30% | 0-55% | 0-35% | 0-5% | 0-5% |
| N-butane | 0-10% | 0-55% | 0-10% | 0-55% | 0-10% |
| Iso-butane | 0-1% | 0-1% | 0-1% | 0-2% | 0-2% |

Other refinery mixed $C_4$ streams, such as those obtained by catalytic cracking of naphthas and other refinery feedstocks, typically have the following composition:

Propylene—0-2 wt %
Propane—0-2 wt %
Butadiene—0-5 wt %
Butene-1—5-20 wt %
Butene-2—10-50 wt %
Isobutene—5-25 wt %
Iso-butane—10-45 wt %
N-butane—5-25 wt %

$C_4$ hydrocarbon fractions obtained from the conversion of oxygenates, such as methanol, to lower olefins more typically have the following composition:

Propylene—0-1 wt %
Propane—0-0.5 wt %
Butadiene—0-1 wt %
Butene-1—10-40 wt %
Butene-2—50-85 wt %
Isobutene—0-10 wt %
N-+iso-butane—0-10 wt %

Any one or any mixture of the above $C_4$ hydrocarbon mixtures can be used in the alkylation process. In addition to linear butenes and butanes, these mixtures typically contain components, such as isobutene and butadiene, which can be deleterious to the alkylation process. For example, the normal alkylation product of isobutene with benzene is tert-butylbenzene which, as previously stated, acts as an inhibitor to the subsequent oxidation step. Thus, prior to the alkylation step, these mixtures may be subjected to butadiene removal and isobutene removal. For example, isobutene can be removed by selective dimerization or reaction with methanol to produce MTBE, whereas butadiene can be removed by extraction or selective hydrogenation to butene-1. Conveniently, the $C_4$ alkylating agent employed in the present process contains less than 1.5 wt %, preferably less than 0.5 wt %, iso-butene and less than 0.1 wt % butadiene.

In addition to other hydrocarbon components, commercial $C_4$ hydrocarbon mixtures typically contain other impurities which could be detrimental to the alkylation process. For example, refinery $C_4$ hydrocarbon streams typically contain nitrogen and sulfur impurities, whereas $C_4$ hydrocarbon streams obtained by oxygenate conversion process typically contain unreacted oxygenates and water. Thus, prior to the alkylation step, these mixtures may also be subjected to one or more of sulfur removal, nitrogen removal and oxygenate removal, in addition to butadiene removal and isobutene removal. Removal of sulfur, nitrogen, oxygenate impurities is conveniently effected by one or a combination of caustic treatment, water washing, distillation, adsorption using molecular sieves and/or membrane separation. Water is also typically removed by adsorption.

Conveniently, the total feed to the alkylation step of the present process contains less than 1000 ppm, such as less than 500 ppm, for example less than 100 ppm, water. In addition, the total feed typically contains less than 100 ppm, such as less than 30 ppm, for example less than 3 ppm, sulfur and less than 10 ppm, such as less than 1 ppm, for example less than 0.1 ppm, nitrogen.

Although not preferred, it is also possible to employ a mixture of a $C_4$ alkylating agent, as described above, and $C_3$ alkylating agent, such as propylene, as the alkylating agent in the present alkylation process so that the alkylation step produces a mixture of cumene and sec-butylbenzene. The resultant mixture can then be processed through oxidation and cleavage, to make a mixture of acetone and MEK, along with phenol, preferably where the molar ratio of acetone to phenol is 0.5:1, to match the demand for bisphenol-A production.

The alkylation catalyst used in the alkylation process is conveniently a crystalline molecular sieve of the MCM-22 family. The term "MCM-22 family material" (or "material of the MCM-22 family" or "molecular sieve of the MCM-22 family" or "MCM-22 family zeolite"), as used herein, includes one or more of:

molecular sieves made from a common first degree crystalline building block unit cell, which unit cell has the MWW framework topology. (A unit cell is a spatial arrangement of atoms which if tiled in three-dimensional space describes the crystal structure. Such crystal structures are discussed in the "Atlas of Zeolite Framework Types", Fifth edition, 2001, the entire content of which is incorporated as reference);

molecular sieves made from a common second degree building block, being a 2-dimensional tiling of such MWW framework topology unit cells, forming a monolayer of one unit cell thickness, preferably one c-unit cell thickness;

molecular sieves made from common second degree building blocks, being layers of one or more than one unit cell thickness, wherein the layer of more than one unit cell thickness is made from stacking, packing, or binding at least two monolayers of one unit cell thickness. The stacking of such second degree building blocks can be in a regular fashion, an irregular fashion, a random fashion, or any combination thereof; and molecular sieves made by any regular or random 2-dimensional or 3-dimensional combination of unit cells having the MWW framework topology.

Molecular sieves of the MCM-22 family include those molecular sieves having an X-ray diffraction pattern including d-spacing maxima at 12.4±0.25, 6.9±0.15, 3.57±0.07 and 3.42±0.07 Angstrom. The X-ray diffraction data used to characterize the material are obtained by standard techniques using the K-alpha doublet of copper as incident radiation and a diffractometer equipped with a scintillation counter and associated computer as the collection system.

Materials of the MCM-22 family include MCM-22 (described in U.S. Pat. No. 4,954,325), PSH-3 (described in U.S. Pat. No. 4,439,409), SSZ-25 (described in U.S. Pat. No. 4,826,667), ERB-1 (described in European Patent No. 0293032), ITQ-1 (described in U.S. Pat. No. 6,077,498), ITQ-2 (described in International Patent Publication No. WO97/17290), MCM-36 (described in U.S. Pat. No. 5,250,277), MCM-49 (described in U.S. Pat. No. 5,236,575), MCM-56 (described in U.S. Pat. No. 5,362,697), UZM-8 (described in U.S. Pat. No. 6,756,030), and mixtures thereof. Molecular sieves of the MCM-22 family are preferred as the alkylation catalyst since they have been found to be highly selective to the production of sec-butylbenzene, as compared with the other butylbenzene isomers. Preferably, the molecular sieve is selected from (a) MCM-49, (b) MCM-56 and (c) isotypes of MCM-49 and MCM-56, such as ITQ-2.

The alkylation catalyst can include the molecular sieve in unbound or self-bound form or, alternatively, the molecular sieve can be combined in a conventional manner with an oxide binder, such as alumina, such that the final alkylation catalyst contains between 2 and 80 wt % sieve.

In one embodiment, the catalyst is unbound and has a crush strength much superior to that of catalysts formulated with binders. Such a catalyst is conveniently prepared by a vapor phase crystallization process, in particular a vapor phase crystallization process that prevents caustic used in the synthesis mixture from remaining in the zeolite crystals as vapor phase crystallization occurs.

Prior to use in the alkylation process, the MCM-22 family zeolite, either in bound or unbound form, may be contacted with water, either in liquid or vapor form, under conditions to improve its sec-butylbenzene selectivity. Although the conditions of the water contacting are not closely controlled, improvement in sec-butylbenzene selectivity can generally be achieved by contacting the zeolite with water at temperature of at least 0° C., such as from about 10° C. to about 50° C., for a time of at least 0.5 hour, for example for a time of about 2 hours to about 24 hours. Typically, the water contacting is conducted so as to increase the weight of the catalyst by 30 to 75 wt % based on the initial weight of the zeolite.

The alkylation conditions conveniently include a temperature of from about 60° C. to about 260° C., for example between about 100° C. and about 200° C., a pressure of 7000 kPa or less, for example from about 1000 to about 3500 kPa, a weight hourly space velocity (WHSV) based on $C_4$ alkylating agent of between about 0.1 and about 50 $hr^{-1}$, for example between about 1 and about 10 $hr^{-1}$, and a molar ratio of benzene to alkylating agent of from about 1 to about 20, preferably about 3 to about 10, more preferably about 4 to about 9.

The reactants can be in either the vapor phase or partially or completely in the liquid phase and can be neat, i.e., free from intentional admixture or dilution with other material, or they can be brought into contact with the zeolite catalyst composition with the aid of carrier gases or diluents such as, for example, hydrogen or nitrogen. Preferably, the reactants are at least partially in the liquid phase.

Using the catalyst and alkylation conditions described above, it is found that the alkylation process is highly selective to sec-butylbenzene. In particular, at a typical benzene conversion rate of 25 wt % and a butene conversion rate greater than 96 wt %, it is found that the alkylated product (i.e., apart from unreacted benzene) generally comprises at least 93 wt %, typically at least 91 wt %, sec-butylbenzene. Depending on the nature of $C_4$ alkylating agent, the alkylated product may contain between about 10 wt % and about 0.01 wt % tert-butylbenzene and between about 0.1 wt % and about 0.01 wt % iso-butylbenzene. Using Raffinate-2 as the $C_4$ alkylating agent, the alkylated product typically contains between about 5 wt % and about 1 wt % tert-butylbenzene and between about 0.2 wt % and about 0.01 wt % iso-butylbenzene.

Although the alkylation step is highly selective towards sec-butylbenzene, the effluent from the alkylation reaction will normally contain some polyalkylated products, as well as unreacted aromatic feed and the desired monoalkylated species. The unreacted aromatic feed is normally recovered by distillation and recycled to the alkylation reactor. The bottoms from the benzene distillation are further distilled to separate monoalkylated product from any polyalkylated products and other heavies. Depending on the amount of polyalkylated products present in the alkylation reaction effluent, it may be desirable to transalkylate the polyalkylated products with additional benzene to maximize the production of the desired monoalkylated species.

Transalkylation with additional benzene is typically affected in a transalkylation reactor, separate from the alkylation reactor, over a suitable transalkylation catalyst, such as a molecular sieve of the MCM-22 family, zeolite beta, MCM-68 (see U.S. Pat. No. 6,014,018), zeolite Y and mordenite. The transalkylation reaction is typically conducted under at least partial liquid phase conditions, which suitably include a temperature of 100 to 300° C., a pressure of 1000 to 7000 kPa, a weight hourly space velocity of 1 to 50 $hr^{-1}$ on total feed, and a benzene/polyalkylated benzene weight ratio of 1 to 10.

Sec-Butyl Benzene Oxidation

The product of the alkylation process described above is intended for use in the production of phenol by the modified Hock process, in which sec-butylbenzene is oxidized to sec-butylbenzene hydroperoxide and the peroxide is cleaved to produce phenol and methyl ethyl ketone. The initial oxidation step is conveniently accomplished by contacting the alkylation product, generally after separation of the unreacted benzene, with an oxygen-containing gas, such as air, in the liquid phase and in the presence of a catalyst. Thus, unlike cumene, atmospheric air oxidation of sec-butylbenzene in the absence of a catalyst is very difficult to achieve. For example, at 110° C. and at atmospheric pressure, sec-butylbenzene is not oxidized, while cumene oxidizes very well under the same conditions. At higher temperature, the rate of atmospheric air oxidation of sec-butylbenzene improves; however, higher temperatures also produce significant levels of undesired by-products.

Suitable sec-butylbenzene catalysts include a water-soluble chelate compound in which multidentate ligands are coordinated to at least one metal from cobalt, nickel, manganese, copper, and iron (See U.S. Pat. No. 4,013,725). More preferably, a heterogeneous catalyst is used. Suitable heterogeneous catalysts are described in U.S. Pat. No. 5,183,945, wherein the catalyst is an oxo (hydroxo) bridged tetranuclear manganese complex and in U.S. Pat. No. 5,922,920, wherein the catalyst comprises an oxo (hydroxo) bridged tetranuclear metal complex having a mixed metal core, one metal of the core being a divalent metal selected from Zn, Cu, Fe, Co, Ni, Mn and mixtures thereof and another metal being a trivalent metal selected from In, Fe, Mn, Ga, Al and mixtures thereof. The entire disclosures of said U.S. patents are incorporated herein by reference.

Other suitable catalysts for the sec-butylbenzene oxidation step are the N-hydroxy substituted cyclic imides described in U.S. Pat. No. 6,720,462 and incorporated herein by reference, such as N-hydroxyphthalimide, 4-amino-N-hydroxyphthalimide, 3-amino-N-hydroxyphthalimide, tetrabromo-N-hydroxyphthalimide, tetrachloro-N-hydroxyphthalimide, N-hydroxyhetimide, N-hydroxyhimimide, N-hydroxytrimellitimide, N-hydroxybenzene-1,2,4-tricarboximide, N,N'-dihydroxy(pyromellitic diimide), N,N'-dihydroxy(benzophenone-3,3',4,4'-tetracarboxylic diimide), N-hydroxymaleimide, pyridine-2,3-dicarboximide, N-hydroxysuccinimide, N-hydroxy(tartaric imide), N-hydroxy-5-norbornene-2,3-dicarboximide, exo-N-hydroxy-7-oxabicyclo[2.2.1]hept-5-ene-2,3-dicarboximide, N-hydroxy-cis-cyclohexane-1,2-dicarboximide, N-hydroxy-cis-4-cyclohexene-1,2dicarboximide, N-hydroxynaphthalimide sodium salt or N-hydroxy-o-benzenedisulphonimide. Preferably, the catalyst is N-hydroxyphthalimide. Another suitable catalyst is N,N',N"-thihydroxyisocyanuric acid.

These materials can be used either alone or in the presence of a free radical initiator and can be used as liquid-phase, homogeneous catalysts or can be supported on a solid carrier to provide a heterogeneous catalyst.

Suitable conditions for the sec-butylbenzene oxidation step include a temperature between about 70° C. and about 200° C., such as about 90° C. to about 130° C., and a pressure of about 0.5 to about 20 atmospheres (50 to 2000 kPa). A basic buffering agent may be added to react with acidic by-products that may form during the oxidation. In addition, an aqueous phase may be introduced, which can help dissolve basic compounds, such as sodium carbonate. The per-pass conversion in the oxidation step is preferably kept below 50%, to minimize the formation of byproducts. The oxidation reaction is conveniently conducted in a catalytic distillation unit and the sec-butylbenzene hydroperoxide produced may be concentrated by distilling off the unreacted sec-butylbenzene prior to the cleavage step.

Selective Dealkylation of Tert- and Iso-Butylbenzene

Even in the presence of catalysts, such as N-hydroxyphthalimide, it is found that tert-butylbenzene and iso-butylbenzene have a deleterious affect on the selectivity of the oxidation process, even at the relatively low levels found in the product of the alkylation process described above. Moreover, tert-butylbenzene and iso-butylbenzene are themselves oxidized at a much slower rate than sec-butylbenzene so that, given the low per-pass conversion of the oxidation process, these impurities will tend to build up the oxidation recycle stream. Since separation by distillation is impractical in view of the similarity in boiling point of these butylbenzene isomers, the present process adopts the novel approach of selectively dealkylating the tert-butylbenzene and iso-butylbenzene in the mixed butylbenzene feed. Since tert-butylbenzene and iso-butylbenzene are dealkylated more rapidly than sec-butylbenzene, it is found that dealkylation allows the concentration of tert-butylbenzene and iso-butylbenzene to be reduced to very low levels without significant loss of the desirable sec-butylbenzene.

The dealkylation step is conducted in the presence of a catalyst system comprising at least a dealkylation catalyst typically comprising at least one of ZSM-5, zeolite beta, zeolite Y, zeolite X and a molecular sieve of the MCM-22 family. Suitable molecular sieves of the MCM-22 family are selected from MCM-22, PSH-3, SSZ-25, ERB-1, ITQ-1, ITQ-2, MCM-36, MCM-49, MCM-56, UZM-8, and mixtures thereof. The dealkylation catalyst system may also comprise at least one hydrogenation metal, such as palladium, ruthenium, nickel, zinc, tin, and cobalt, with palladium being particularly advantageous. Generally, the amount of hydrogenation metal present in the catalyst is between about 0 and about 10 wt %, such as between about 0.1 and about 5 wt %, of the catalyst. The hydrogenation metal can be supported directly on the molecular sieve or can be supported, partially or totally, on an inorganic oxide separate from the molecular sieve. Suitable inorganic oxides include oxides of Groups 2, 4, 13 and 14 of the Periodic Table of Elements, such as alumina, titania, and/or zirconia. As used herein, the numbering scheme for the Periodic Table Groups is as disclosed in Chemical and Engineering News, 63(5), 27 (1985).

Suitable conditions for the dealkylation step include a temperature of about 130° C. and about 260° C., a pressure of about 100 kPa to about 1000 kPa and hydrogen to hydrocarbon molar ratio of 0 to about 1000. Any suitable reactor can be employed for the dealkylation step, although a catalytic distillation reactor is generally preferred.

The dealkylation step selectively converts the tert-butylbenzene and iso-butylbenzene in the feed to benzene and iso-butene, with the latter reacting with the butylbenzenes in the feed to produce dibutylbenzenes or, in the presence of hydrogen, being reduced to iso-butane. The dealkylation effluent can then be fractionated into a $C_{10}$ stream rich in sec-butylbenzene which can be fed to the oxidation step, a benzene stream, a $C_{14}$+ stream, and a $C_4$ stream. By removing any unreacted isobutene in the fractionation step, the benzene can be recycled to the initial alkylation stage, whereas the isobutene and isobutane have value as precursors to iso-octane and the dibutylbenzenes in the $C_{14}$+ stream can be used as fuel blending stocks.

Alternatively, the dealkylation catalyst system may include an oligomerization catalyst, which may be the same as or different from the dealkylation catalyst, so that the iso-butene generated by dealkylation of the tert-butylbenzene and iso-butylbenzene is at least partially oligomerized to a $C_8$+ olefin stream, which again can be separated from the benzene and sec-butylbenzene in the dealkylation effluent by fractionation.

In one embodiment, the dealkylation step is conducted on at least a portion of the effluent of the alkylation process, generally after removal of unreacted benzene and any dibutylated product.

In a further embodiment, the dealkylation step is conducted on at least a portion of the recycle stream remaining after separation of the sec-butylbenzene hydroperoxide from the effluent of the oxidation process. Conveniently, the recycle stream is subjected to an initial hydrotreating step to remove any remaining oxygenates, before the recycle steam is contacted with the dealkylation catalyst.

In yet a further embodiment, both the alkylation effluent and the oxidation recycle stream are subjected to selective alkylation steps.

Depending on the level of these impurities in the original butylbenzene feed, the dealkylation step allows the concentration of each of the tert-butylbenzene and iso-butylbenzene in the feed to be reduced to less than 5 wt %, generally less than 1.5 wt %, typically less than 0.15 wt %. At the same time the conversion of sec-butylbenzene is generally less than 1 wt %, typically less than 0.15 wt %.

Hydroperoxide Cleavage

The final step in the conversion of the sec-butylbenzene into phenol and methyl ethyl ketone involves cleavage of the sec-butylbenzene hydroperoxide, which is conveniently effected by contacting the hydroperoxide with a catalyst in the liquid phase at a temperature of about 20° C. to about 150° C., such as about 40° C. to about 120° C., a pressure of about 50 to about 2500 kPa, such as about 100 to about 1000 kPa and a liquid hourly space velocity (LHSV) based on the hydroperoxide of about 0.1 to about 100 $hr^{-1}$, preferably about 1 to about 50 $hr^{-1}$. The sec-butylbenzene hydroperoxide is preferably diluted in an organic solvent inert to the cleavage reaction, such as methyl ethyl ketone, phenol or sec-butylbenzene, to assist in heat removal. The cleavage reaction is conveniently conducted in a catalytic distillation unit.

The catalyst employed in the cleavage step can be a homogeneous catalyst or a heterogeneous catalyst.

Suitable homogeneous cleavage catalysts include sulfuric acid, perchloric acid, phosphoric acid, hydrochloric acid and p-toluenesulfonic acid. Ferric chloride, boron trifluoride, sulfur dioxide and sulfur trioxide are also effective homogeneous cleavage catalysts. The preferred homogeneous cleavage catalyst is sulfuric acid.

A suitable heterogeneous catalyst for use in the cleavage of sec-butylbenzene hydroperoxide includes smectite clay, such as an acidic montmorillonite silica-alumina clay, as described in U.S. Pat. No. 4,870,217, the entire disclosure of which is incorporated herein by reference.

When a stream is described as being "rich" in a specified species, it is meant that no other species is present (on a weight percentage basis) in amounts equal to or greater than that specified.

The invention will now be more particularly described with reference to the following non-limiting Examples and the accompanying drawings.

Example 1

Dealkylation of Sec-Butylbenzene (SBB)

A MCM-49 catalyst (100 wt % zeolite) was dried at 260° C. for a minimum of 2 hours before testing. 0.5 grams of the catalyst was loaded between two 0.25-inch (0.6 cm) layers of inert, 8-grit quartz particles that were previously dried at 120° C. until loaded into the stationary sample basket of the reactor. 126 grams of a sec-butylbenzene blend was added to a 300 ml batch autoclave reactor. The sample basket assembly was installed into the body of the autoclave reactor and sealed. The reactor was evacuated and purged twice with nitrogen to ensure the elimination of air from the head space.

The reactor contents were mixed at 1000 rpm with a vertically positioned impeller located in the center of the stationary sample basket. The reactor was heated to 170° C. for about 30 minutes using a programmable autoclave controller to maintain constant ramp rate and temperature. Reaction time zero was recorded from the point at which temperature and pressure targets (170° C., 446 kPa) were attained and stable. At the end of 1-hour, ~1-cc of product was extracted from the reactor. The total reaction period for this evaluation was 4 hours. At the end of the reaction period, the run was discontinued, the reactor cooled to ambient conditions and the total liquid product retained. Only incremental samples extracted throughout the run were GC analyzed. This includes the fourth and final ~1-cc sample taken under reaction conditions. Product analysis by GC was based on the assumption that composition of light components in the vapor phase was identical to those dissolved in the liquid phase. This analysis was performed using an HP 6890 GC equipped with a DB-1 column (60M, 0.25 mm ID, 1 micro meter film thickness) and a flame ionization detector (FID) detector. The results are shown in FIG. 1.

Example 2

Dealkylation of Tert-Butylbenzene (TBB)

The process of Example 1 was repeated but with the sec-butylbenzene blend being replaced by 126 grams of a tert-butylbenzene blend. Again the results are shown in FIG. 1 and demonstrate that, whereas there was substantially no conversion of the sec-butylbenzene after the 4 hour test of Example 1, about 12 wt % of the tert-butylbenzene was dealkylated over the period of the test of Example 2.

Example 3

Dealkylation of SBB/TBB Mixture at Different Temperatures

Figure 2:
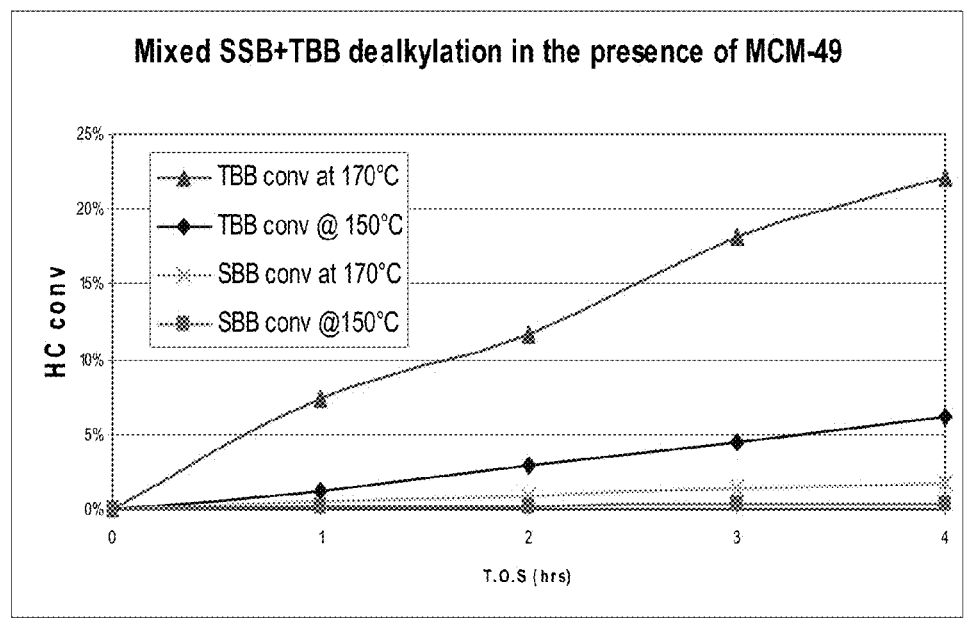
FIG. 2 is graph comparing the rates of conversion of sec-butylbenzene and tert-butylbenzene with time on stream for the dealkylation of a mixture of sec-butylbenzene and tert-butylbenzene in the presence of a MCM-49 catalyst in accordance with the process of Example 3.

The process of Example 1 was again repeated but with the sec-butylbenzene blend being replaced by a mixture of 120 grams of sec-butylbenzene and 6 grams of tert-butylbenzene. In addition, in Example 3 two separate dealkylation runs were conducted, one at 170° C. as in the case of Examples 1 and 2 and another at 150° C. The results are shown in FIG. 2 and demonstrate that at 150° C., sec-butylbenzene conversion was negligible after the 4 hour test, whereas 5 to 6 wt % of tert-butylbenzene was converted. At 170° C., sec-butylbenzene conversion was only 1 to 2 wt % after the 4 hour test, whereas 22 wt % of tert-butylbenzene was converted.

Example 4

Hydrodealkylation of SBB/TBB over Pd/MCM-49

A catalyst was prepared by combining MCM-49 with a 1.25 wt % solution of polyvinyl alcohol (PVA) to target 0.5 wt % PVA on a solids basis and mulled. Additional water was then added to target 42% solids and the mixture was mulled and extruded into 1/16" quadrulobe extrudates. The extrudate was calcined in nitrogen for 3 hours at 950° F. (510° C.), ammonium exchanged with 1N ammonium nitrate solution, and calcined in 60% air for 6 hours at 1000° F. (540° C.). The extrudate was then impregnated via incipient wetness to 0.1 wt % Pd with tetraamine palladium(II) nitrate followed by drying at 250° F. (121° C.) and calcination in full air for 3 hours at 580° F. (304° C.).

0.5 gram of the resultant catalyst was loaded between two 0.25-inch layers of inert, 8-grit quartz particles that were previously dried at 120° C. until loaded into the stationary sample basket of the reactor. A mixture of 120 gram of sec-butyl benzene and 6 gram tert-butyl benzene was added to a 300 ml batch autoclave reactor. The sample basket assembly was installed into the body of the autoclave reactor and sealed. The reactor was evacuated and purged twice with hydrogen to ensure the elimination of air from the head space. The batch reactor was then pressured to about 200 psig (1480 kPa) with hydrogen to ensure proper sealing and absence of leaks. Pressure was reduced to about 25 psig (274 kPa) starting pressure.

Reactor contents were mixed at 1000 rpm with a vertically positioned impeller located in the center of the stationary sample basket. The reactor was heated to 170° C. for about 30 minutes using a programmable autoclave controller to maintain constant ramp rate and temperature. After reaching temperature, reactor vapor pressure increased to about 40 psig (377 kPa). Then, 40 psig hydrogen was fed by regulator to the system. Reaction time zero was recorded from the point at which temperature and pressure targets (170° C., 40 psig) were attained and stable. At the end of 1-hour, ~1-cc of product was extracted from the reactor. The total reaction period for this evaluation was 4 hours. At the end of the reaction period, the run was discontinued, the reactor cooled to ambient conditions and the total liquid product retained. Only incremental samples extracted through out the run were GC analyzed. This includes the fourth and final ~1-cc sample taken under reaction conditions.

Figure 3:
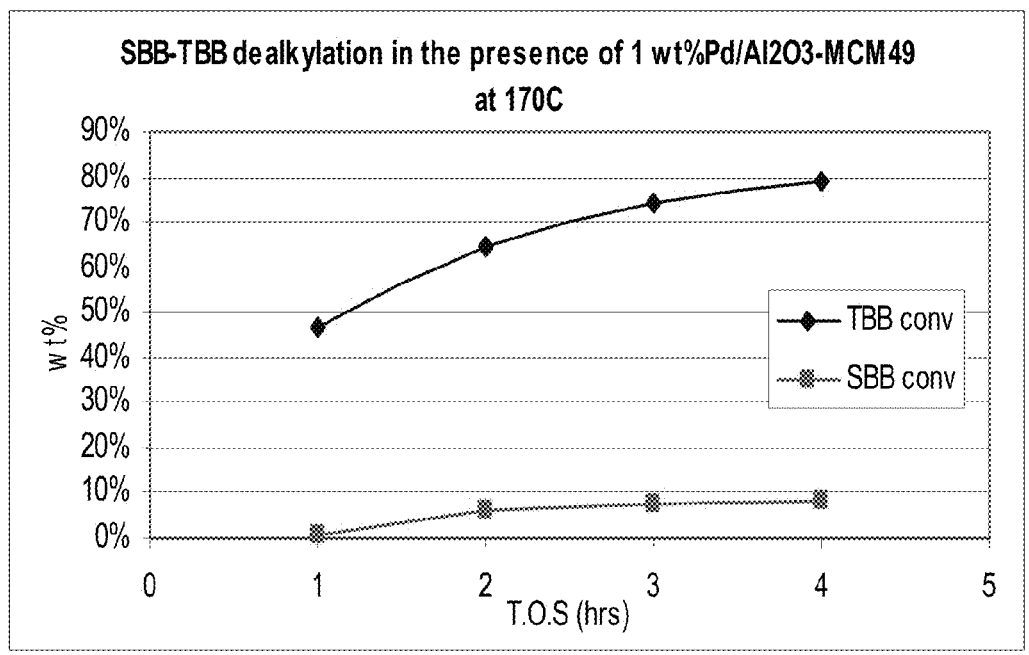
FIG. 3 is graph comparing the rates of conversion of sec-butylbenzene and tert-butylbenzene with time on stream for the dealkylation of a mixture of sec-butylbenzene and tert-butylbenzene in the presence of hydrogen and a catalyst comprising MCM-49 and 1 wt % Pd on alumina in accordance with the process of Example 4.

Product analysis by GC was based on the assumption that composition of light components in the vapor phase was identical to those dissolved in the liquid phase. This analysis was performed using an HP 6890 GC equipped with a DB-1 column (60M, 0.25 mm ID, 1 micro meter film thickness) and an FID detector. The results are shown In FIG. 3 and demonstrate that, although about 8 wt % of the sec-butylbenzene had been dealkylated after the 4 hour test, the conversion of tert-butylbenzene over the same period was almost 80 wt %.

While the present invention has been described and illustrated by reference to particular embodiments, those of ordinary skill in the art will appreciate that the invention lends itself to variations not necessarily illustrated herein. For this reason, then, reference should be made solely to the appended claims for purposes of determining the true scope of the present invention.

The invention claimed is:

1. A process for reducing the level of tert-butylbenzene in a mixed butylbenzene feed comprising tert-butylbenzene and sec-butylbenzene, the process comprising contacting the feed under dealkylation conditions with a catalyst system comprising a dealkylation catalyst whereby the tert-butylbenzene is selectively dealkylated to produce an effluent stream which comprises benzene and which has a lower concentration of tert-butylbenzene than said feed, wherein said contacting under dealkylation conditions is conducted in the presence of hydrogen and the catalyst system further comprises a hydrogenation metal such that iso-butene produced in the selective dealkylation of said tert-butylbenzene is at least partially hydrogenated to produce iso-butane.

2. The process of claim 1, wherein said feed contains up to 50 wt % tert-butylbenzene and said effluent stream contains less than 5 wt % tert-butylbenzene.

3. The process of claim 1, wherein said feed also comprises iso-butyl benzene and said contacting selectively dealkylates the iso-butylbenzene such that said effluent stream has a lower concentration of iso-butyl benzene than said feed.

4. A process for producing phenol and methyl ethyl ketone, the process comprising:
   (a) contacting benzene and a $C_4$ olefin stream under alkylation conditions and in the presence of an alkylation catalyst to produce an alkylation effluent comprising sec-butylbenzene, iso-butyl benzene and tert-butylbenzene;
   (b) contacting at least a portion of said alkylation effluent under dealkylation conditions with a catalyst system comprising a dealkylation catalyst whereby iso-butylbenzene and tert-butylbenzene in said at least a portion of said alkylation effluent are selectively dealkylated to produce a dealkylation effluent which comprises benzene and unreacted sec-butylbenzene and which has a lower concentration of iso-butylbenzene and tert-butylbenzene than said at least a portion of said alkylation effluent, wherein said contacting under dealkylation conditions is conducted in the presence of hydrogen and the catalyst system further comprises a hydrogenation metal such that iso-butene produced in the selective dealkylation of said tert-butylbenzene is at least partially hydrogenated to produce iso-butane;
   (c) oxidizing at least a portion of the sec-butylbenzene in said dealkylation effluent to produce an oxidation effluent comprising sec-butylbenzene hydroperoxide;
   (d) cleaving at least a portion of the sec-butylbenzene hydroperoxide produced in said oxidizing (c) to produce phenol and methyl ethyl ketone; and
   (e) recycling at least part of the benzene from said dealkylation effluent to said contacting (a).

5. The process of claim 4, wherein the alkylation effluent produced in (a) further comprises unreacted benzene and said unreacted benzene is separated from said alkylation effluent before said contacting (b).

6. The process of claim 5, wherein said unreacted benzene separated from said alkylation effluent is recycled to said contacting (a).

7. The process of claim 4, and further comprising fractionating said dealkylation effluent to remove $C_4$ hydrocarbons therefrom and to separate said dealkylation effluent into a sec-butylbenzene-rich portion, which is oxidized in said oxidizing (c), and a benzene-rich portion, which is recycled to said contacting (a).

8. A process for producing phenol and methyl ethyl ketone, the process comprising:
   (a) contacting benzene and a $C_4$ olefin stream under alkylation conditions and in the presence of an alkylation catalyst to produce an alkylation effluent comprising sec-butylbenzene, iso-butylbenzene and tert-butylbenzene;
   (b) oxidizing part of the sec-butylbenzene in said alkylation effluent to produce an oxidation effluent comprising sec-butylbenzene hydroperoxide, unreacted sec-butylbenzene, iso-butylbenzene and tert-butylbenzene;
   (c) separating at least part of said sec-butylbenzene hydroperoxide from said oxidation effluent to leave a recycle stream comprising unreacted sec-butylbenzene, iso-butylbenzene and tert-butylbenzene;

(d) cleaving at least a portion of the sec-butylbenzene hydroperoxide separated in said oxidizing (c) to produce phenol and methyl ethyl ketone;
(e) contacting at least a portion of said recycle stream under dealkylation conditions with a catalyst system comprising a dealkylation catalyst whereby iso-butylbenzene and tert-butylbenzene in said at least a portion of said recycle stream are selectively dealkylated to produce a further effluent stream which comprises benzene and unreacted sec-butylbenzene and which has a lower concentration of iso-butylbenzene and tert-butylbenzene than said at least a portion of said recycle stream, wherein said contacting under dealkylation conditions is conducted in the presence of hydrogen and the catalyst system further comprises a hydrogenation metal such that iso-butene produced in the selective dealkylation of said tert-butylbenzene is at least partially hydrogenated to produce iso-butane;
(f) recycling at least part of the benzene from said further effluent stream to said contacting (a); and
(g) recycling at least part of the unreacted sec-butylbenzene from said further effluent stream to said oxidizing (b).

9. The process of claim 8, wherein said recycle stream is divided into a first portion, which is subjected to said contacting (e), and a second portion, which is recycled directly to said oxidizing (b).

10. The process of claim 9, and further comprising:
(h) hydrotreating said first recycle stream portion to remove oxygenates therefrom prior to said contacting (e).

11. The process of claim 8, and further comprising:
(i) fractionating said further effluent stream to remove $C_4$ hydrocarbons therefrom and to produce at least a benzene-rich fraction for said recycling (f) and a sec-butylbenzene-rich fraction for said recycling (g).

12. The process of claim 11, wherein said fractionating (i) also produces a heavy fraction comprising dibutylbenzenes.

13. The process of claim 1, wherein the dealkylation catalyst comprises at least one of ZSM-5, zeolite beta, zeolite Y, zeolite X and a molecular sieve of the MCM-22 family.

14. The process of claim 1, wherein the dealkylation catalyst comprises at least one molecular sieve of the MCM-22 family selected from MCM-22, PSH-3, SSZ-25, ERB-1, ITQ-1, ITQ-2, MCM-36, MCM-49, MCM-56, UZM-8, and mixtures thereof.

15. The process of claim 1, wherein said catalyst system further comprises an oligomerization catalyst such that isobutene produced in the selective dealkylation of said tert-butylbenzene is at least partially oligomerized.

16. The process of claim 1, wherein the dealkylation conditions include a temperature of 130° C. and 260° C., a pressure of 100 kPa to 1000 kPa and hydrogen to hydrocarbon molar ratio of 0 to 1000.

* * * * *